United States Patent
Tellier et al.

[11] 3,943,152
[45] Mar. 9, 1976

[54] METHOD FOR PREPARING AZINES

[75] Inventors: Pierre Tellier, Oullins; Jean-Pierre Schirmann, Brignais; Henri Mathais, Ste. Foy-les-Lyon; Francis Weiss, Pierre Benite, all of France

[73] Assignee: Produits Chimiques Ugine Kuhlmann, Paris, France

[22] Filed: Mar. 14, 1973

[21] Appl. No.: 341,057

[30] Foreign Application Priority Data
Mar. 24, 1972 France .............................. 72.10328

[52] U.S. Cl. ........ 260/345.1; 260/345.9; 260/566 B
[51] Int. Cl.² .............. C07C 109/14; C07C 109/16
[58] Field of Search .......... 260/566 B, 465.5, 345.9, 260/345.1

[56] References Cited
UNITED STATES PATENTS
2,870,206   1/1959   Meyer et al. ..................... 260/566 B Primary Examiner—Gerald A. Schwartz
Attorney, Agent, or Firm—Pennie & Edmonds

[57] ABSTRACT

A method is disclosed for preparing symmetrical azines of the formulas

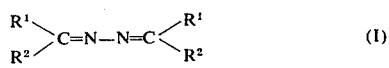 (I)

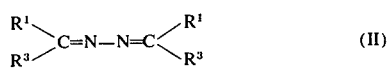

(II)

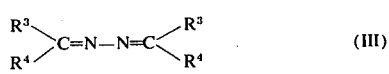

(III)

and unsymmetrical azines of the formulas

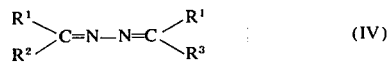 (IV)

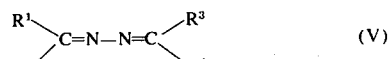

(V)

and mixtures of azines (I), (II) and (IV) and (I), (III) and (V) wherein $R^1$, $R^2$, $R^3$ and $R^4$ each is a hydrogen atom, a straight chain alkyl radical of from 1 to 12 carbon atoms, a branched chain alkyl radical or unsubstituted or alkyl substituted cycloalkyl radical of from 3 to 12 carbon atoms, a hydrocarbon radical of from 6 to 12 carbon atoms containing an aromatic nucleus; further provided that $R^1$ and $R^2$ can be the same or different radicals, and $R^3$ and $R^4$ are the same or different radicals and each are different from $R^1$ and $R^2$; or $R^1$ and $R^2$ or $R^1$ and $R^3$ or $R^3$ and $R^4$ bonded to the same carbon atom together form an unsubstituted or aliphatic substituted alkylene radical of from 3 to 11 carbon atoms, each of the aforesaid radicals being unsubstituted or substituted with one or more radicals which are stable in the medium in which the azines are produced.

The method comprises reacting ammonia, hydrogen peroxide and a carbonyl compound of the formula

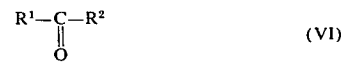 (VI)

alone or together with a different carbonyl compound

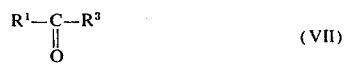 (VII)

or

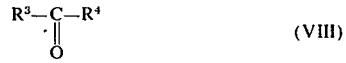 (VIII)

wherein $R^1$, $R^2$, $R^3$ and $R^4$ each have the same meaning defined above in the presence of an amide or an imide of a carboxylic acid having an ionization constant greater than $5 \times 10^{-5}$ or of a di-, tri- or tetracarboxylic acid of which at least one of the carboxylic acid functions has an ionization constant greater than $5 \times 10^{-5}$ (corresponding to a pK less than about 4.3) to produce the azine or mixture of azines.

3 Claims, No Drawings

METHOD FOR PREPARING AZINES

BACKGROUND OF THE INVENTION

I. Field of the Invention

This invention relates to a method for preparing symmetrical azines as well as mixtures containing symmetrical and unsymmetrical azines.

II. Description of the Prior Art

Aldehydes are known to react with ammonia in a complex manner giving rise to various addition, condensation or polymerization products (see for example, *The Chemistry of the Carbon-Nitrogen Bond*, S. Patai, Interscience, London, 1970, page 67) or with hydrogen peroxide to form unstable peroxide products and to give rise, after reaction with ammonia and hydrogen peroxide, to peroxidic compounds (see for example, *J. Chem. Soc.* 1969, p. 2678).

Moreover, it is known that ammonia, a ketone and hydrogen peroxide react together to produce aminoperoxides (see for example, *J. Chem. Soc.* 1969, C, page 2663) and in the presence of such catalysts as tungstic or molybdic acid, to an oxime (see for example, *J. Gen. Chem.* (U.S.S.R.) 1960, 30, p. 1635), or in the presence of the ammonium salts or hydroxides of metals of Group Ia and IIa of the Periodic Table of the Elements, result in azines (see copending application Ser. No. 267,921, filed June 30, 1972.

Another method for preparing azines comprising the oxidation of ammonia in the presence of a ketone or aldehyde by means of an oxidizing medium of hydrogen peroxide and cyanogen or a nitrile is fully disclosed in commonly assigned copending U.S. application Ser. No. 152,413, filed June 11, 1971.

Another method for preparing azines comprises oxidizing a secondary alcohol in the liquid phase to form peroxide products of the auto-oxidation of the alcohol and subsequently reacting the peroxidic products with ammonia in the presence of cyanogen or a nitrile. This method is fully disclosed in commonly assigned pending U.S. application Ser. No. 230,038, filed Feb. 28, 1972. Still another method of preparing azines comprises reacting ammonia, hydrogen peroxide and carbonyl compounds in the presence of a carboxylic ester as disclosed in commonly assigned pending U.S. application Ser. No. 340,763 filed Mar. 13, 1973.

SUMMARY OF THE INVENTION

It has been surprisingly discovered that symmetrical azines of the formulas

(I)

(II)

(III)

and unsymmetrical azines of the formulas

(IV)

(V)

can be conveniently prepared in good yields by reacting ammonia, hydrogen peroxide and a carbonyl compound of the formula

(VI)

alone or together with a different carbonyl compound

(VII)

or

(VIII)

wherein $R^1$, $R^2$, $R^3$ and $R^4$ each have the same meaning defined above in the presence an amide or an imide of a carboxylic acid having an ionization constant greater than $5 \times 10^{-5}$ or of a di-, tri- or tetra-carboxylic acid of which at least one of the carboxylic acid functions has an ionization constant greater than $5 \times 10^{-5}$ (corresponding to a pK less than about 4.3) to produce the azine or mixture of azines.

When a single carbonyl compound (VI) is reacted according to the method of this invention, a symmetrical azine having the formula

(I)

is produced.

When, for example, both $R^1$ and $R^2$ of carbonyl compound (VI) is hydrogen, the carbonyl compound is formaldehyde and the azine resulting from this method is the symmetrical aldazine, formaldazine, which has the formula

When only one of the substituents is hydrogen, the resulting aldazine, for example, has the formula

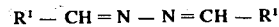

wherein the substituent $R^1$ is not hydrogen.

When neither of the substituents of the carbonyl compound (VI) is hydrogen, the carbonyl compound (VI) is a ketone and the resulting azine is a symmetrical ketazine of the formula

(I)

wherein none of the substituents $R^1$ and $R^2$ is hydrogen.

When in addition to carbonyl compound (VI), a different carbonyl compound (VII) is simultaneously reacted according to the method of this invention, a mixture of symmetrical and unsymmetrical azines of the formulas

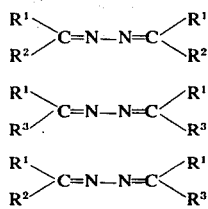

is produced.

And if in addition to carbonyl compound (VI), a different carbonyl compound (VIII) is simultaneously reacted according to the method of this invention, a mixture of symmetrical and unsymmetrical azines of the formulas

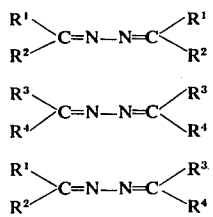

is produced.

When both carbonyl compounds (VI) and (VII) are aldehydes, a mixture of symmetrical and unsymmetrical aldazines will be obtained. Similarly, if both carbonyl compounds (VI) and (VII) or (VI) and (VIII) are ketones, a mixture of symmetrical and unsymmetrical ketazines will be produced. And if one of the carbonyl compounds (VI), (VII) or (VIII) is an aldehyde and the other carbonyl compound which is being simultaneously reacted is a ketone, the method of this invention will yield a mixture of azines containing a symmetrical aldazine, a symmetrical ketazine and an unsymmetrical azine possessing the characteristics of both an aldazine and a ketazine.

Any number of different aldehydes and/or ketones may be reacted according to the method of this invention to yield mixtures of azines, the number and amount of which are present in the mixture being made to depend upon the number, amount and nature of the carbonyl compounds reacted.

DESCRIPTION OF THE PREFERRED EMBODIMENTS

The carbonyl compounds of this invention can contain ethylenic bonds and substituents which are stable in the reaction medium such as chlorine, bromine, and fluorine atoms and nitro, hydroxy, alkoxy, carboxylic acid, carboxylic amide, esters or nitrile groups.

Some examples of aldehydes conforming to formulas (VI), (VII) or (VIII) which are advantageously employed in the process of this invention include formaldehyde, acetaldehyde, propionaldehyde, butyraldehyde, isobutyraldehyde, n-pentanal, pivalaldehyde, oenanthal, 2-ethylhexanal, 3-$\Delta$ tetrahydrobenzaldehyde, hexahydrobenzaldehyde, 5-norbornene-2-carboxaldehyde, tetrahydropyran-2-carboxaldehyde, benzaldehyde, the monochlorobenzaldehydes, p-nitrobenzaldehyde, anisaldehyde, $\beta$-chloropropionaldehyde and $\beta$-methoxypropionaldehyde.

Some examples of ketones conforming to formula (VI), (VII) or (VIII) which are advantageously employed in the method of this invention include acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyclooctanone, cyclodecanone and cyclododecanone.

The carboxylic acid amides and imides which are useful in the method of this invention have been observed to play a role as effective oxidation coreactants for the preparation of the azines herein through the reaction of ammonia and one or several carbonyl compounds with hydrogen peroxide. It has been established that the carboxylic acid amide or imide is converted into the ammonium salt of the same carboxylic acid during the reaction. Although the reaction mechanism is not fully known, the reaction (illustrating the use of an amide) can be theorized to take place as follows:

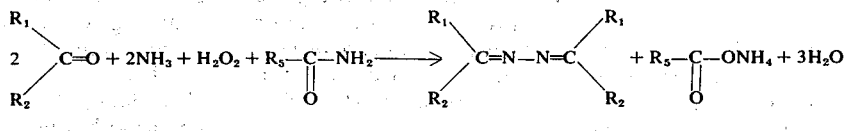

The reaction is general in nature and does not depend upon the particular nature of the carboxylic acid amide or imide employed but it has been noted that the reaction proceeds very slowly with amides or imides having ionization constants less than about $5 \times 10^{-5}$. In this case, the known reactions of ammonia and carbonyl compounds with hydrogen peroxide or the simple decomposition of the latter take place in the basic reaction medium instead of the desired reaction.

It is therefore advantageous to employ the amides or imides of carboxylic acids having an ionization constant greater than $5 \times 10^{-5}$ in order to provide a suitable rate of reaction and good selectivity for the desired reaction. The useful amides and imides can be derived from the monocarboxylic or polycarboxylic acids such as the di-, tri and tetra- carboxylic acids of which at least one of the carboxylic acid functions has an ionization constant greater than $5 \times 10^{-5}$ (corresponding to a pK less than about 4.3).

The acids responding to this requirement can be selected from amongst the monoacids $R_5COOH$ and the polyacids $R'_5(COOH)_x$.

$R_5$ of the monoacids $R_5COOH$ represents (a) a hydrogen atom or a halogenated alkyl radical having from 1 to 8 carbon atoms and possessing up to $n$ halogen atoms, at least one of which is in the $\alpha$ or $\beta$ position with respect to the carboxylic group, $n$ being the total number of hydrogen atoms in the corresponding unsubstituted alkyl radical; (b) a hydroxylated alkyl radical having from 1 to 8 carbon atoms and possessing from 1 to 5 hydroxyl groups bonded to different carbon atoms with at least one hydroxyl group in the $\alpha$ or $\beta$ position with respect to the carboxylic group; (c) a halogenated alkyl radical having from 1 to 8 carbon atoms and possessing a combined total of from 2 to 6 halogen atoms and hydroxyl groups of which one halogen atom or hydroxyl group is in the α or β position with respect to the carboxylic group and no hydroxyl group is bonded to a carbon atom possessing a halogen atom or second hydroxyl group; or (d) a phenyl, phenylmethyl or diphenylmethyl radical which is unsubstituted or ring substituted with from 1 to 5 halogen atoms or methyl, hydroxyl, methoxy, nitro or carboxylic acid groups.

$R'_5$ of the polyacids $R'_5(COOH)_x$ can represent (a) a single bond in which case $x$ is equal to 2; (b) an alkylidene radical having from 1 to 8 carbon atoms in which case $x$ is equal to 2; (c) an alkylene or alkylenyl radical having from 2 to 5 carbon atoms which is unsubstituted or substituted with from 1 to 4 halogen atoms, hydroxyl groups or any combination thereof with no hydroxyl group being bonded to a carbon atom possessing a halogen atom or second hydroxyl group in which case $x$ is equal to 2, 3 or 4; (d) an aromatic radical of valence $x$ in which $x$ is equal to 2, 3 or 4 and which can be substituted with up to $6-x$ halogen atoms or methyl, hydroxy, methoxy or nitro groups or any combination thereof.

In the above definition, the term "halogen" is intended to be understood according to its commonly recognized meaning namely, the term refers to the fluorine, chlorine, bromine and iodine atoms.

Some examples of amides and imides which can advantageously be employed in the method of this β-bromopropionamide,α,β-dibromopropionamide, include: formamide, monochloroacetamide, monobromoacetamide, dichloroacetamide, trichloroacetamide, trifluoroacetamide, α-chloropropionamide, β-chloropropionamide, α,α-dichloropropionamide, α,β-dichloropropionamide, α-bromopropionamide, α-chloroisobutyramide, perfluorobutyramide, glycolamide, lactamide, β-hydroxypropionamide, glyceramide, α-hydroxy-β-chloropropionamide, α-chloro-β-hydroxypropionamide, glycolamide, phenylacetamide, o-chlorophenylacetamide, m-chlorophenylacetamide, p-chlorophenylacetamide, o-bromophenylacetamide, m-bromophenylacetamide, p-bromophenylacetamide, o-fluorophenylacetamide, m-fluorophenylacetamide, p-fluorophenylacetamide, o-nitrophenylacetamide, m-nitrophenylacetamide, p-nitrophenylacetamide, dinitro-2,4 phenyl acetamide, diphenylacetamide, benzamide, o-toluamide, m-toluamide, o-chlorobenzamide, m-chlorobenzamide, p-chlorobenzamide, o-bromobenzamide, m-bromobenzamide, p-bromobenzamide, o-fluorobenzamide, m-fluorobenzamide, p-fluorobenzamide, o-iodobenzamide, m-iodobenzamide, p-iodobenzamide, pentachlorobenzamide, pentafluorobenzamide, o-nitrobenzamide, m-nitrobenzamide, p-nitrobenzamide, o-nitro-o'-methylbenzamide, salicylamide, m-hydroxybenzamide, p-hydroxybenzamide, o-methoxybenzamide, m-methoxybenzamide, the monoamides, the diamides or the cyclic imides of the following di- tri, and tetracids: oxalic, malonic, methylethylmalonic, diethylmalonic, succinic, α,α-dichlorosuccinic, maleic, tartaric, malic, α,α'-dichloroglutaric, α-hydroxyadipic, citric, itaconic, citraconic, o-phthalic, isophthalic, terephthalic, trimellitic, pyromellitic and tetrachloro-o-phthalic acids.

Formamide is especially advantageous for use herein due to its low molecular weight and its relatively low cost.

The reaction components are reacted in liquid media and are mixed one after the other or as various combinations. For example, the reaction components can be separately or simultaneously introduced into the reactor on a continuous or batch-wise basis or the hydrogen peroxide can be added to a mixture containing the ammonia, the carbonyl compound or mixture thereof and the carboxylic acid amide or imide; the ammonia or ammonia solution can be added to a mixture containing the hydrogen peroxide, the carbonyl compound or mixture thereof and the amide or imide; the amide or imide can be added to a mixture containing ammonia, hydrogen peroxide and carbonyl compound(s) and/or the corresponding aminoperoxides; or the hydrogen peroxide can be reacted with the carbonyls to provide a mixture of one or several known peroxidic products and this mixture can then be reacted with ammonia and the amide or imide. It is advantageous to employ a solvent or blend of solvents to maintain a homogenous reaction medium or to assure at least a partial solubilization of the reactants. Examples of solvents which can be used for this purpose include the saturated alcohols having 1 to 6 carbon atoms such as methanol, ethanol, n-propanol, isopropanol, n-butanol, 2-butanol, isobutanol, tert-butanol, the amyl alcohols and cyclohexanol.

The temperature of the reaction can be maintained over a wide range but it is advantageous to maintain a temperature of from about −20° to 100°C and at a pressure equal to or greater than atmospheric pressure, up to 10 atmospheres if such is necessary to maintain the reactants in solution.

The reaction components can be employed in stoichiometric quantities according to the above equation but it is also possible to use other proportions in which case, it is advantageous to react up to a ten-fold excess of one or several of the reactants. It is generally preferable not to use an excess of hydrogen peroxide so as to avoid or minimize secondary decomposition reactions or undesirable oxidation products.

It can be advantageous to add one or more known and conventional stabilizers for peroxidic compositions or substances which exercise a buffering action on the pH of the reaction medium. For example, from about 0.01 to 1.0% by weight of the reaction medium of phosphoric acid, pyrophosphoric acid, citric acid, nitrilotriacetic acid, ethylenediaminetetraacetic acid or the alcaline metal or ammonium salts of the aforesaid acids can be used.

Upon completion of the reaction, the azines can be recovered from the medium by means of known and conventional techniques including extraction with a non-miscible solvent, fractional distillation or a combination of these two methods.

The azines of this invention are useful as intermediates in the preparation of many important products, and in particular, are useful for preparing hydrazine and hydrazine salts by hydrolysis according to known and conventional methods. Hydrolysis of the azines releases the carbonyl compounds which can then be recycled for preparing additional quantities of azines according to the method of this invention.

The following examples are illustrative of the method of this invention. Although the examples employ but a single carbonyl compound resulting in symmetrical azines it is understood that the same procedures can be followed except that two or more different aldehydes or ketones or one or more aldehydes and ketones are reacted to result in a mixture of symmetrical and unsymmetrical azines as hereinbefore described.

EXAMPLE 1

14.5 gm of acetone (0.25 moles), 5 gm of water, 65 gm of methanol, 5 gm of a 68% by weight solution of hydrogen peroxide (0.1 moles) and 0.25 gm of the disodium salt of ethylenediaminetetraacetic acid (EDTA) were placed in a reactor and thereafter 5.1 gm ammonia (0.3 moles) were dissolved in the reaction mixture. The reaction mixture was heated to 50°C and 4.5 gm of formamide (0.1 moles) were added to the mixture over 10 minutes. The temperature was maintained at 50°C for 3½ hours during which a slight stream of ammonia, about 0.1 moles/hours, was introduced into the medium. The acetoneazine present in the reaction medium was measured chemically and by gas phase chromatography. 6.2 gm of acetoneazine (0.055 moles) had formed corresponding to a yield of 55% by comparison to the hydrogen peroxide.

After leaving the mixture for 24 hours at 20°C, the reaction was allowed to continue and the final yield of acetoneazine then attained 70%.

EXAMPLE 2

Example 1 was substantially repeated except that twice the amount of formamide (9.0 gm; 0.2 moles) was employed. After reacting for 3½ hours at 50°C, the reaction medium contained 8.5 gm of acetoneazine (0.076 moles) corresponding to a yield of 76%; after 6½ hours at 50°C, the reaction medium contained 9.0 gm of acetoneazine (0.08 moles) corresponding to a yield of 80% based on the amount of hydrogen peroxide used.

EXAMPLE 3

Example 1 was substantially repeated except that methanol was replaced with the same weight of water. After the reaction medium has reacted for 3½ hours at 50°C, analysis indicated that 6.1 gm of acetoneazine (0.054 moles) had formed thus corresponding to a yield of 54% based on the amount of hydrogen peroxide used.

EXAMPLE 4

Example 1 was repeated except that the formamide was replaced with 14.7 gm of o-phthalimide (0.1 moles). After the reaction medium had reacted for 5 hours at 50°C, analysis indicated that 4.3 gm of acetoneazine (0.038 moles) had formed thus corresponding to a yield of 38% based on the amount of hydrogen peroxide used.

EXAMPLE 5

Example 1 was substantially repeated except that the formamide was replaced with 9.9 gm of succinimide (0.10 moles) which were introduced in the reaction mixture containing the other reactants over a period of 10 minutes at 50°C. After the reaction medium had reacted for 7 hours at 50°C, analysis indicated that 3.52 gm of acetoneazine (0.0314 moles) had formed thus corresponding to a yield of 31.4% based on the amount of hydrogen peroxide used.

EXAMPLE 6

Example 1 was substantially repeated except that the formamide was replaced with 9.35 gm of monochloroacetamide (0.10 moles) introduced into the other reactants over 10 minutes at 50°C. After 7 hours at 50°C, 4.3 gm of acetoneazine (0.0385 moles) corresponding to a yield of 38.5% based on the hydrogen peroxide used was present in the medium.

EXAMPLE 7

Example 1 was substantially repeated except that the formamide was replaced with 8.9 gm of lactamide (0.10 moles) introduced into the other reactants over 10 minutes at 50°C. After 8 hours at 50°C, analysis indicated the presence of 0.85 gm of acetoneazine (0.0076 moles) in the reaction medium thus corresponding to a yield of 7.6% based on the amount of hydrogen peroxide used.

EXAMPLE 8

Example 1 was substantially repeated except that the acetone was replaced with 24.5 gm of cyclohexanone (0.25 moles). After 5 hours of reaction at 50°C, 8.35 gm of cyclohexanoneazine (0.435 moles) had formed in the reaction medium corresponding to a yield of 43.5% based on the amount of hydrogen peroxide used.

We claim:

1. A method for preparing azines which consists of reacting
   a. ammonia;
   b. hydrogen peroxide;
   c. a carbonyl compound selected from formaldehyde, acetaldehyde, propionaldehyde, butyraldehyde, isobutyraldehyde, n-pentanal, pivalaldehyde, oenanthal, 2-ethylhexanal, 3-Δ-tetrahydrobenzaldehyde, hexahydrobenzaldehyde, 5-norbornene-2-carboxaldehyde, tetrahydropyran-2-carboxaldehyde, benzaldehyde, monochlorobenzaldehyde, p-nitrobenzaldehyde, anisaldehyde, β-chloropropionaldehyde, β-methoxypropionaldehyde, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, isophorone, cycloheptanone, cyclooctanone, cyclodecanone and cyclododecanone, and mixtures thereof; and
   d. an amide or imide selected from formamide, monochloroacetamide, monobromoacetamide, dichloroacetamide, trichloroacetamide, trifluoroacetamide, α-chloropropionamide, β-chloropropionamide, α,α-dichloropropionamide, α,β-dichloropropionamide, α-bromopropionamide, β-bromopropionamide, α,β-dibromopropionamide, α-chloroisobutyramide, perfluorobutyramide, glycolamide, lactamide, β-hydroxypropionamide, glyceramide, α-hydroxy-β-chloropropionamide, α-chloro-β-hydroxypropionamide, glycolamide, phenylacetamide, chlorophenylacetamide, bromophenylacetamide, fluorophenylacetamide, nitrophenylacetamide, 2,4-dinitrophenylacetamide, diphenylacetamide, benzamide, o-toluamide, m-toluamide, chlorobenzamide, bromobenzamide, fluorobenzamide, iodobenzamide, pentachlorobenzamide, pentafluorobenzamide, nitrobenzamide, o-nitro-o'-methylbenzamide, salicylamide, m-hydroxybenzamide, p-hydroxybenzamide, o-methoxybenzamide, m-methoxybenzamide, and the amic acids, diamides and imides of oxalic, malonic, methylethylmalonic, diethylmalonic, succinic, α,α-dichlorosuccinic, maleic, tartaric, malic, α,α'-dichloroglutaric, α-hydroxyadipic, citric, itaconic, citraconic, o-phthalic, isophthalic, terephthalic, trimellitic, pyromellitic and tetrachloro-o-phthalic acids,
and recovering the azine or mixture of azines from the reaction medium.

2. The method of claim 1 wherein the reaction is carried out in the presence of a solvent comprising a saturated alcohol of from 1 to 6 carbon atoms.

3. The method of claim 1 wherein the reaction is carried out at a temperature between about −20° and 100°C.

* * * * *

UNITED STATES PATENT OFFICE
CERTIFICATE OF CORRECTION

Patent No. 3,943,152  Dated March 9, 1976

Page 1 of 2

Inventor(s) Pierre Tellier et al

It is certified that error appears in the above-identified patent and that said Letters Patent are hereby corrected as shown below:

Column 5, lines 30 through 65 should read as shown on the attached sheet.

Some examples of amides and imides which can advantageously be employed in the method of this invention include: formamide, monochloroacetamide, monobromoacetamide, dichloroacetamide, trichloroacetamide, trifluoroacetamide, α-chloropropionamide, β-chloropropionamide, α,α-dichloropropionamide, α,β-dichloropropionamide, α-bromopropionamide, β-bromopropionamide, α,β-dibromopropionamide, α-chloroisobutyramide, perfluorobutyramide, glycolamide, lactamide, β-hydroxypropionamide, glyceramide, α-hydroxy-β-chloropropionamide, α-chloro-β-hydroxypropionamide, glycolamide, phenylacetamide, o-chlorophenylacetamide, m-chlorophenylacetamide, p-chlorophenylacetamide, o-bromophenylacetamide, m-bromophenylacetamide, p-bromophenylacetamide, o-fluorophenylacetamide, m-fluorophenylacetamide, p-fluorophenylacetamide, o-nitrophenylacetamide, m-nitrophenylacetamide, p-nitrophenylacetamide, dinitro-2,4 phenyl acetamide, diphenylacetamide, benzamide, o-toluamide, m-toluamide, o-chlorobenzamide, m-chlorobenzamide, p-chlorobenzamide, o-bromobenzamide, m-bromobenzamide, p-bromobenzamide, o-fluorobenzamide, m-fluorobenzamide, p-fluorobenzamide, o-iodobenzamide, m-iodobenzamide, p-iodobenzamide, pentachlorobenzamide, pentafluorobenzamide, o-nitrobenzamide, m-nitrobenzamide, p-nitrobenzamide, o-nitro-o'-methylbenzamide, salicylamide, m-hydroxybenzamide, p-hydroxybenzamide, o-methoxybenzamide, m-methoxybenzamide, the monoamides, the diamides or the cyclic imides of the following di- tri, and tetracids: oxalic, malonic, methylethylmalonic, diethylmalonic, succinic, α,α-dichlorosuccinic, maleic, tartaric, malic, α,α'-dichloroglutaric, α-hydroxyadipic, citric, itaconic, citraconic, o-phthalic, isophthalic, terephthalic, trimellitic, pyromellitic and tetrachloro-o-phthalic acids.

Signed and Sealed this

*twenty-ninth* Day of *June 1976*

[SEAL]

*Attest:*

RUTH C. MASON
*Attesting Officer*

C. MARSHALL DANN
*Commissioner of Patents and Trademarks*